(12) United States Patent
Margraf et al.

(10) Patent No.: US 9,926,383 B2
(45) Date of Patent: Mar. 27, 2018

(54) BIOCOMPATIBLE THREE DIMENSIONAL MATRIX FOR THE IMMOBILIZATION OF BIOLOGICAL SUBSTANCES

(75) Inventors: Stefan Margraf, Frankfurt am Main (DE); Martin Scholz, Oberursel (DE)

(73) Assignee: LEUKOCARE AG, Munich (DE)

( * ) Notice: Subject to any disclaimer, the term of this patent is extended or adjusted under 35 U.S.C. 154(b) by 657 days.

(21) Appl. No.: 12/299,382

(22) PCT Filed: May 7, 2007

(86) PCT No.: PCT/EP2007/004016
§ 371 (c)(1),
(2), (4) Date: Nov. 3, 2008

(87) PCT Pub. No.: WO2007/128550
PCT Pub. Date: Nov. 15, 2007

(65) Prior Publication Data
US 2009/0269778 A1    Oct. 29, 2009

(30) Foreign Application Priority Data
May 5, 2006  (EP) .................................... 06009343

(51) Int. Cl.
*G01N 33/53* (2006.01)
*C07K 17/14* (2006.01)
*C07K 17/02* (2006.01)

(52) U.S. Cl.
CPC .............. *C07K 17/14* (2013.01); *C07K 17/02* (2013.01)

(58) Field of Classification Search
None
See application file for complete search history.

(56) References Cited

U.S. PATENT DOCUMENTS

| | | | |
|---|---|---|---|
| 4,925,818 A | | 5/1990 | Schneider et al. |
| 5,077,210 A | * | 12/1991 | Eigler et al. ................... 435/176 |
| 5,266,471 A | * | 11/1993 | Schmitt ........................... 435/178 |
| 5,283,034 A | * | 2/1994 | Okrongly et al. ............... 422/22 |
| 5,691,152 A | * | 11/1997 | Burton et al. ................... 435/7.5 |
| 5,730,933 A | * | 3/1998 | Peterson .......................... 422/22 |
| 5,760,130 A | | 6/1998 | Johnston et al. |

FOREIGN PATENT DOCUMENTS

| | | |
|---|---|---|
| EP | 1 571 204 A | 9/2005 |
| JP | S6187700 | 5/1986 |
| JP | S63230088 | 9/1988 |
| JP | 1-228454 | 4/1990 |
| JP | 01-239449 | 4/1991 |
| JP | 01-317389 | 8/1991 |
| JP | 04-19561 | 1/1992 |
| JP | 04-121188 | 9/1993 |
| JP | 04-218371 | 2/1994 |
| JP | 05-219952 | 3/1995 |
| JP | H1181790 | 3/1999 |
| JP | 2000-502883 | 3/2000 |
| JP | 2000-514778 | 11/2000 |
| JP | 11-299882 | 4/2001 |
| JP | 2003-503736 | 1/2003 |
| JP | 2005505324 | 2/2005 |
| JP | 2005505552 | 2/2005 |
| WO | 9640297 | 12/1996 |
| WO | 9717435 | 5/1997 |
| WO | 9717436 | 5/1997 |
| WO | 9926674 | 6/1999 |
| WO | WO 01/0601 A | 1/2001 |
| WO | WO 01/02858 A | 1/2001 |
| WO | WO 01/14425 A | 3/2001 |
| WO | WO 02/46756 A | 6/2002 |
| WO | 03020324 A2 | 3/2003 |
| WO | 03020325 A2 | 3/2003 |
| WO | 03030949 A1 | 4/2003 |
| WO | WO 04/033720 A | 4/2004 |

OTHER PUBLICATIONS

Dow Corning, "A Guide to Silane Solutions," 2005.*
Knecht et al., "Automated Microarray System for the Simultaneous Detection of Antibiotics in Milk," Anal. Chem., 2004, vol. 76, No. 3, pp. 646-654.*
Scholz et al., "Fas/FasL interaction: A novel immune therapy approach with immobilized biologicals," Medicinal Research Reviews, 2005, vol. 25, No. 3, pp. 331-342.*
Utley et al., "Effect of Albumin and Mannitol on Organ Blood Flow, Oxygen Delivery, Water Content, and Renal Function during Hypothermic Hemodilution Cardiopulmonary Bypass," Ann. Thorac. Surg., 1982, vol. 33, pp. 250-257.*
A print-out retrieved from http://en.wikipedia.org/wiki/Freeze-drying#Properties_of_freeze-dried_products on Aug. 9, 2013.*
A print-out retrieved from http://en.wikipedia.org/wiki/Agar on Aug. 9, 2013.*
A print-out retrieved from http://en.wikipedia.org/wiki/Drying on Mar. 17, 2015.*
A print-out from http://www.porex.com/technologies/materials/porous-plastics/ retrieved on Aug. 7, 2014.*
Leukocare Press Release, "Start of clinical trial for Leukocyte Inhibition Module (LIM)," Oct. 2005.*
A print-out retrieved from http://www.differencebetween.net/science/biology-science/difference-between-dulbecco%e2%80%99s-pbs-and-pbs/#ixzz4KvN7IxHB on Sep. 21, 2016.*
Print-out retrieved from http://www.sigmaaldrich.com/content/dam/sigma-aldrich/docs/Sigma/Formulation/d5773for.pdf on Sep. 21, 2016.*

(Continued)

*Primary Examiner* — Galina M Yakovleva
(74) *Attorney, Agent, or Firm* — Gavrilovich, Dodd & Lindsey LLP (57) ABSTRACT

The present invention relates to a method of producing a solid coated carrier carrying biological material. Furthermore, the invention relates to a solid coated carrier to which biological material is attached and uses of the solid coated carrier for the preparation of a medical product. Moreover, the invention provides a method for the contacting, filtration or cleaning of blood, lymph or liquor cerebrospinalis of a patient, a method for the diagnosis of a disease and a diagnostic composition.

29 Claims, 3 Drawing Sheets

(56) References Cited

OTHER PUBLICATIONS

Mandenius, C. et al., "The interaction of Proteins and Cells with Affinity Ligands Covalently Coupled to Silicon Surfaces as Monitored by Elipsometry," Analytical Biochemistry, 1984, pp. 106-114, vol. 137, No. 1.
Piehler J. et al., "A high-density poly(ethylene glycol) polymer brush for immobilisation on glass-type surfaces," Biosensors and Bioelectronics, Nov. 2000, pp. 473-481, vol. 15, No. 9-10.
Jerry Fireman, Modernizing Sterlization Standards, Orthopedic Design & Technology, Nov.-Dec. 2008.
Schobert, B. et al., "Stabilization of Phosphorylase b Against Temperature-Induced Inactivation and Denaturation by Ionic and Non-Ionic Solutes", Hoppe-Seyler's Z. Physiol. Chem., Bd., 361, S. 211-356, Mar. 1980.
Stadtman et al., "Free radical-mediated oxidation of free amino acids and amino acid residues in proteins", Amino Acids, 2003, 25; 207-218.
Weetall, Howard H., "Preparation and Characterization of Antigen and Antibody Adsorbents Covalently Coupled to an Inorganic Carrier", Biochem. J., 1970, 117, 257-261.
Weetall, Howard H., "Preparation Immobilized Proteins Covalently Coupled Through Silane Coupling Agents to Inorganic Supports", Applied Biochemistry and Biotechnology, vol. 41, 1993, pp. 157-188.
Leukocare in the Press—Leukocare AG, Martinsried, Munich, Germany (Dec. 4, 2013).

\* cited by examiner

BIOCOMPATIBLE THREE DIMENSIONAL MATRIX FOR THE IMMOBILIZATION OF BIOLOGICAL SUBSTANCES

CROSS REFERENCE TO RELATED APPLICATIONS

This application is filed as a U.S. National Stage Application under 35 U.S.C. § 371 and claims priority to International Application No. PCT/EP07/04016, filed May 7, 2007 in English, which appliction claims prioirty to EP Application NO. 06009343.2, filed on May 5, 2006, the disclsoures of which are incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

Field of the Invention

The present invention relates to a method of producing a solid coated carrier carrying biological material. Furthermore, the invention relates to a solid coated carrier to which biological material is attached and uses of the solid coated carrier for the preparation of a medical product. Moreover, the invention provides a method for the contacting, filtration or cleaning of blood, lymph or liquor cerebrospinalis or parts thereof of a patient, a method for the diagnosis of a disease and a diagnostic composition.

Description of Realted Art

The systemic application e.g. of monoclonal antibodies or other molecules is an important and growing field for the treatment of tumor patients, metabolic disorders, immune diseases or other diseases. However, the systemic application of these molecules is extremely expensive and is frequently associated with severe side effects and increased mortality. Moreover, the fate of the injected biologicals is often ill defined and severe side effects can not be foreseen in the individual patient.

An option for the application of novel therapeutic procedures is the use of (medical) devices with immobilized antibodies. This procedure has the advantage over the standard therapies to use the functional properties of the antibody without the possibly detrimental effects of a systemic application. Therefore, severe side effects frequently observed using antibodies systemically are not seen using this safe procedure based on a (medical) device. A transient or permanent application of such a device within the blood stream aiming to manipulate the physiology, the immune system, immune cells or other constituents of the blood, or floating tumor cells, with immobilized, highly defined quantities of biological material on a defined surface, which could e.g. imply a defined density of the biological material within a defined volume would circumvent the heavy burden of systemic application of certain drugs.

Therapies are described in the art in which TNFα is inactivated by the use of inactivating antibodies like Remicade®. However, the simple administration of such antibodies to a patient is known to be associated with severe, even deadly, side-effects (blindness, shock, allergic reaction and the like). Moreover, the administration of full antibodies or fragments or derivatives thereof requires a humanization and/or other modifications of the antibodies in order to reduce or circumvent an inactivation of the antibodies by an immune reaction of the human patient against the antibodies.

A further approach described in the art is known under the name "TheraSorb®" (Miltenyi Biotech GmbH, Bergisch-Gladbach, Germany); see R. Bambauer et al., Ther Apher Dial. 2003, 7(4):382-90 and G. Wallukat et al., International Journal of Cardiology, 1996, 54 (2):191-195. TheraSorb® is used to remove LDL-cholesterol, immunoglobulins, immune complexes, antibody fragments or fibrinogen. The apheresis columns used in this method contain sepharose with coupled polyclonal antibodies. The procedure requires cell separation to deliver plasma to the column. This is a major disadvantage of the system, because this is an extravagant expenditure. The flow rate is low and therefore only small amounts of plasma are treated. The system is also very expensive due to its complexity.

The above discussion demonstrates that the methods and systems available so far for the treatment of the recited diseases are either associated with severe side effects or rather burdensome to implement. Thus, the technical problem underlying the present invention was to provide means and methods which enable the treatment of patients with biological material such as cells and proteins, which improve this situation. The solution to this technical problem is achieved by the embodiments characterized in the claims.

BRIEF SUMMARY OF THE INVENTION

Accordingly, the present invention provides in a first embodiment a method of producing a solid coated carrier carrying a biological material, comprising the steps of:
(a) incubating a solid carrier with a solution comprising 0.1 to 10% (w/w) or (v/v) of at least one silane and subsequently removing the solution;
(b) attaching the biological material to the carrier by incubating the carrier with a preferably buffered aqueous solution containing the biological material and subsequently removing the aqueous solution; and
(c) incubating the carrier in an aqueous solution comprising one or more substances selected from (poly)peptides, amino acids, starch, sugars, phosphates, polyalcohols, polyethyleneglycols (PEGs) or a mixture thereof.

Steps (a), (b) and (c) are carried out in the above described order.

BRIEF DESCRIPTION OF THE SEVERAL VIEWS OF THE DRAWINGS

FIG. 1:

Scheme of the coating procedure for the immobilization of biological material. Exemplified is the procedure for biological material such as antibodies or cells (or fragments) and their functional maintenance under stress conditions. A dark filled oval surrounded by a larger unfilled oval represents an antigen presenting cell (APC).

FIG. 2:

Flow cytometric dot blot analyses which depicts the experimental result described in the appended example 1. The analysis reveals the maintenance of antibody-mediated apoptosis induction after EO-sterilization.

FIG. 3:

Schematic design of an example for a therapeutic toxin trap (e.g. a dioxin trap). The exemplified design allows a low blood flow and priming volume. Thus, it may also be used in diverse catheter systems such as Sheldon catheters, e.g. after/during trauma, shock and sepsis and other settings in critical care.

FIG. 4:

Schematic depiction of an example for a (medical) device consisting of a plastic housing carrying a polyurethane foam with immobilized antibodies (e.g. against CD95). Neutrophils can transiently adhere to the antibodies embedded by the coating. The binding of the antibody can trigger a signal for the inactivation of the neutrophils.

DETAILED DESCRIPTION OF THE INVENTION

A variety of documents is cited throughout this specification. The disclosure content of said documents including manufacturer's manuals is herewith incorporated by reference in its entirety.

The term "solid carrier" defines in the context of the invention a carrier of solid material. The material of the carrier may be either of compact or porous structure. As described herein below, it is preferred that the carrier is of a material selected from the group consisting of glass, polyurethane, polyester, polysulfone, polyethylene, polypropylene, polyacrylic, polyacrylonitrile, polyamide, PMMA, fleece wadding, open porous foam plastic or glass and reticular plastic or glass and structures derived from marine sponges (porifera).

The term "preferably buffered" according to the present invention refers to a solution which is preferably buffered.

The term "biological material" describes in the context of the invention material isolated from living or dead organisms or parts thereof or producible in artificial biological systems and chemically modified derivatives thereof. An example for an artificial biological system comprises means for the in vitro synthesis of nucleic acid molecules or (poly)peptides or the production by recombinant DNA technologies. As described in detail herein below examples for such biological material comprise eukaryotic cells, fragments of eukaryotic cells, prokaryotes, fragments of prokaryotes, archaebacteria, fragments of archaebacteria, viruses and viral fragments. The recited fragments of eukaryotic cells, prokaryotes, archaebacteria and viruses comprise one or more (poly)peptides, oligonucleotides, polynucleotides and polysaccharides or any combination thereof. (Poly)peptides, oligonucleotides, polynucleotides and polysaccharides are alternatively and still encompassed by the term biological material, if they do not find a counterpart in nature and are, e.g. (semi)synthetically or recombinantly produced (see below).

The term "(poly)peptide" as used herein describes a group of molecules which comprise the group of peptides, as well as the group of polypeptides. The group of peptides consists of molecules up to 30 amino acids, the group of polypeptides consists of molecules with more than 30 amino acids. In accordance with the invention, the group of "polypeptides" comprises "proteins". Also in line with the definition the term "(poly)peptide" describes fragments of proteins. The definition of the term further comprises polypeptides which are dimers, trimers and higher oligomers, i.e. consisting of more than one string of amino acid molecules (chains of linked amino acids). As noted herein above, proteins are also understood as fragments of eukaryotic cells, prokaryotes, archaebacteria and viruses in case said proteins are isolated from eukaryotic cells, prokaryotes, archaebacteria and viruses. The term also applies to (poly)peptides which are produced by recombinant DNA technologies or other technologies employing e.g. cells for the production of the recited compounds.

The term "oligonucleotides" describes in the context of the invention nucleic acid molecules consisting of at least ten and up to 30 nucleotides. The term "polynucleotides" describes nucleic acid molecules consisting of more than 30 nucleotides. Oligonucleotides and polynucleotides described herein may be DNA, RNA, PNA and the like. The group of molecules subsumed under polynucleotides also comprise complete genes or chromosomes and fragments thereof. Also included by said definition are vectors such as cloning and expression vectors.

The term "polysaccharide" defines in the context of the invention polymers consisting of two or more than two saccharides and thus includes molecules otherwise known in the art as oligosaccharides. Said polysaccharides may consist of chains of branched or non-branched saccharides.

The term "silane" is used in the context of the invention in line with the definition of the International Union of Pure and Applied Chemistry (IUPAC) and describes a group of compounds consisting of a silicon matrix and hydrogen. A silane according to this definition may be branched (iso- and neo-silanes) or non-branched (n-silanes).

The term "body fluid" defines in the context of the inventions fluids derivable in samples from a patient, preferably a human patient. Examples for such body fluids comprise blood, lymph or liquor cerebrospinal or parts thereof, e.g. blood plasma or liquid fractions comprising albumin, as well as enriched leukocytes (e.g. from leukapheresis).

The term "patient" as used throughout the present invention comprises ill or diseased as well as healthy subjects. A patient in accordance with the present invention is any person who receives medical attention, care, or treatment. The person is most often but not always ill or injured and, if so, in need of treatment by a physician or other medical professional. In other terms, the term "patient" is interchangeably used with "subject" which may or may not be ill. The subject can be an animal, preferably a mammal, most preferably a human. In accordance with the above, a patient is also, for example, a healthy human who is, on an acute or routine basis, diagnosed for a disease or health status. In other terms, the invention may be used to find out whether a patient suffers from a certain disease (or a combination of diseases), is prone to develop such a disease or combination thereof or not.

The removal of the solutions is understood as a qualitative removal of the solution. Thus, the solution is removed at least to a degree where the remaining solution does not significantly change the quality of a solution used in a subsequent step of the method of the invention. The removal may be effected e.g. by suction, e.g. by using a conventional pump to which a pipette may be attached, and the like, compression or blowing. Optionally, such steps are combined and may be further combined with air drying. Preferably, the solution is removed in volume to at least 95% such as at least 98% or at least 99%, 99.5% or 99.8%.

The term "incubating" refers to an incubation under conditions that allow the compounds recited in steps (a) to (c) to attach to the carrier or to a layer of molecules as mentioned in steps (a) and/or (b) attached to the carrier, optionally via an indirect binding. Incubation conditions include those where incubations are effected from 20 minutes to 12 hours depending on the step and the temperature. In general, antibodies are incubated for 1 hour at 37° C., which is the maximum temperature where IgM antibodies are stable. IgG antibodies can be incubated to up to 50° C. The temperature range may be from 4° C. to 50° C., preferably 20 to 37° C., depending on the step and the incubation time. It is preferred that, in step (a), incubation is effected for a period of 20 minutes at room temperature, in step (b) for 1 hour at 37° C. and in step (c) for 1 hour at room temperature. It is understood that in order to expedite the procedure or to improve the result, the incubation times and temperatures can be varied according to the substances used in the incubation. For example, if methanol is used as solvent in step (a), the temperature should be kept low at around 20° C., e.g. from about 15 to about 25° C., in order not to let the methanol evaporate.

The skilled artisan is aware that the term "room temperature" can imply different temperatures depending on the location and the outside temperature. It usually ranges between 17 and 23° C.

The solution recited in step (a) of the method of the invention may be an aqueous or a non-aqueous solution. An aqueous solution in step (a) according to the method of the invention may, in addition to the silane, comprise diluted proteins and further diluted components such as sugars or alcohols. A preferred protein in this context is albumin. Albumin, in accordance with the present invention comprises albumins from animals, preferably mammals, more preferably from humans, and from plant seeds. Albumins form the major constituent of serum in mammals. Further examples of albumins according to the present invention are α-lactalbumin and ovalbumin in animals, legumelin from peas, leucosin from wheat, rye or barley or legumelin from legumes. In case of potential allergens, it is preferred that the albumin is hydrolyzed, especially to enhance the compatibility with the human or other animal body. The same holds true for the non-aqueous solution in an alternative embodiment of step (a).

In the context of the present invention, the term "aqueous solvent" is not limited to (but includes) $H_2O$ but extended to hydrophilic solvents mixable with water thus able to form a uniform phase.

Examples for aqueous solvents comprise, but are not limited to $H_2O$, methanol, ethanol or higher alcohols or mixtures thereof. Examples for non-aqueous solvents comprise, but are not limited to dimethylsulfoxide (DMSO), benzene, toluene, xylene and ethylbenzene, or aliphatic solvents like pentane, hexane, heptane or mixtures thereof.

It is preferred that the solvent of the solution in step (a) is $H_2O$, methanol, ethanol or mixtures thereof, dimethylsulfoxide (DMSO), benzene, toluene, xylene and ethylbenzene or pentane, hexane, heptane or mixtures thereof. The most preferred solvent of the solution of step (a) is methanol or ethanol. Correspondingly, a solution means a solution comprising a solvent and an aqueous solution means a solution comprising a hydrophilic solvent.

According to the invention the concentration of the at least one silane in step (a) of the method is in a range between 0.1 and 10% (w/w) or (v/v), wherein this range simultaneously defines the concentration of all silanes in the solution. In other terms, the contribution of all silanes together, if more than one silane is employed, is in the range of 0.1 to 10% (w/w) or (v/v). Preferably, the concentration is in a range of 0.5 to 5% (w/w) or (v/v).

The attachment of the biological material to the solid carrier according to step (b) of the method of the invention is understood as a fixation of the material on the carrier. The fixation may be effected via a direct binding of the biological material to the solid carrier. Alternatively, the fixation may be effected via an indirect binding via a third compound such as a layer of one or more silanes covering the solid carrier. The term "covering" according to the present invention comprises full coverage as well as partial coverage of the solid carrier. In both alternatives the binding can be a binding via a covalent or a non-covalent bond. In line with the invention a covalent bond can be achieved e.g. by a chemical reaction between the biological material and a carrier material or between the silane (coating the carrier material) and the biological material. In the latter case the silane acts like a molecular bridge. Examples for non-covalent binding comprise weak bonds such as van-der-Waal's bonds or other polar bonds. Such non-covalent bonds occur e.g. between (poly)peptides and a solid carrier with a polyethylene surface.

Preferably the aqueous solution for the attachment of biological material such as e.g. antibodies is buffered and of low salt content. A low salt content according to the present invention is defined as a salt concentration of 0.9% (w/w) or less, preferably less than 0.2% (w/w). Generally, but not exclusively for the type IgG and IgY a more basic buffer, e.g. made of 15 mM sodium carbonate and 35 mM sodium hydrogencarbonate in water (ph 9) is useful whereas that for the attachment of IgM a more neutral buffer (pH 7.0 to 7.4), e.g. a phosphate buffer like PBS, is favorable. Due to the incubation of the carrier to which the biological material in step (b) is attached in an aqueous solution according to step (c) of the method of the invention the biological material is embedded in a coating layer/coating matrix. By the embedding the accessible surface of the biological material is minimized.

The aqueous solution of step (c) preferably is of low salt content as defined above. It can optionally be buffered.

The steps of the method of invention may be affected in batches in which the respective solutions are exchanged.

Figure 1:
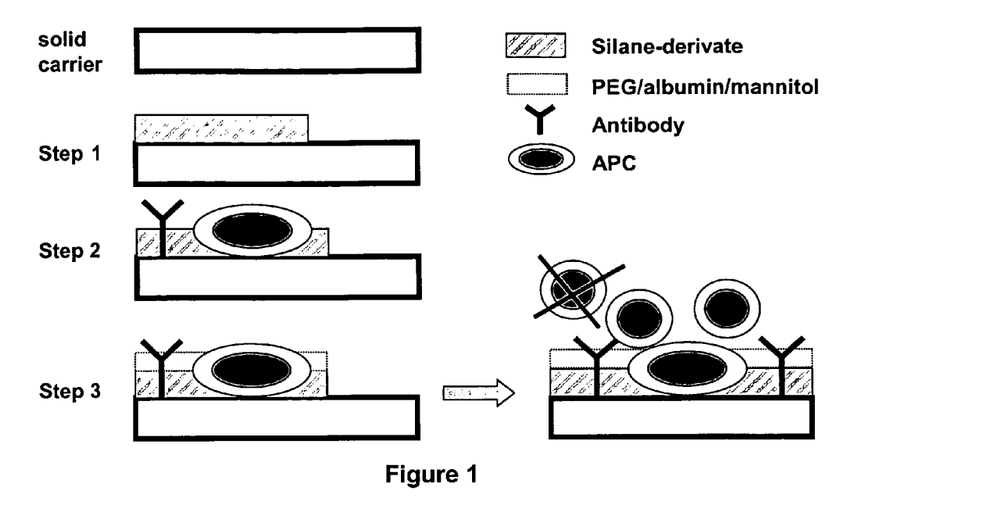

The method of the present invention provides solid carriers, which are coated with a matrix, into which the recited biological material is embedded. One embodiment of such a solid coated carrier comprising embedded biological material is exemplified in the cross-section depicted in the scheme of FIG. 1.

Solid carriers produced by the method of the invention can be used in therapy and diagnosis.

Such therapies comprise the detoxification of body fluids from toxins such as dioxin, botulism toxin, tetanus toxin, LPS, septic poisons etc. The carriers may also be useful in the treatment of bacterial or viral diseases. One envisaged alternative application of the carriers produced by the method of the invention is the use in a therapy which requires the stimulation, elimination or removal of certain cells of a patient. An elimination of a specific population of cells may be e.g. indicated in the treatment of proliferative diseases (e.g. general in the treatment of cancer and particularly in the treatment of minimal residual cancer), autoimmune diseases or a treatment of diseases followed by organ transplantation. A stimulation of a specific population of cells may be envisaged e.g. in the treatment of a disease which is effected by the activation of cells of the immune system which are suitable, after stimulation, to eliminate a specific population of diseased cells. A further therapy approach makes use of solid coated carriers into which genetically or otherwise manipulated (e.g. differentiated by incubation with synthetic or natural compounds like cytokines, butyric acid, phorbol myristate acetate or all-transretinoic acid or physical manipulation like heat shock, cryopreservation, centrifugation) recombinant donor cells or non-manipulated donor cells are embedded. The embedded cells may secrete compounds such as hormones which reduce or heal endocrinal or metabolic disorders. Examples for the above described therapies are described in detail herein below. The therapy approaches may comprise an in vivo as well as an ex vivo application of the carrier produced by the method of the invention in the context of a (medical) device. Accordingly, a device comprising the solid coated carrier can be implanted into a patient for an in vivo application. For an ex vivo application a device comprising the solid coated carrier can be connected with the circulation of the body liquid to be treated. Blood derived from an artery or a vein of a patient may be e.g. led through such device and subsequently piped back into the patient (connection with the blood stream). Alternatively, samples of a body fluid may be incubated with the carrier in vitro. In a subsequent step of the latter treatment the body fluid can be reintroduced into the body of a patient.

Diagnostic applications of the solid carriers produced by the method of the invention are e.g. diagnostic methods which require the detection of toxins or specific cell populations in a body fluid. A diagnostic application using a solid coated carrier produced in accordance with the invention can be useful in a quantitative detection of toxins or specific cell populations. In such applications carriers may be employed to which a single type of biological material such as an antibody is attached. An incubation of such carrier with a defined volume of the body fluid from a patient will allow to quantitatively extrapolate an/the amount of the compound on the complete body of the patient after the analysis of the amount of the compound detected by the attached biological material in the sample. A qualitative detection of toxins or specific cell populations can be effected e.g. by the use of carriers to which many different types of biological materials are attached to. After incubation of the solid coated carrier with a body fluid from a patient the person skilled in the art can analyze which toxins or cell populations are specifically bound/detected by the attached biological material in the sample.

In the above described therapy approaches the embedded biological material will have a therapeutic impact e.g. on the blood, the lymph or the liquor without releasing the attached/immobilized biological material into the body fluid due to the fixation of the biological material on the solid carrier. It is preferred that no significant amount of the attached/immobilized biological material will be released into the body fluid. Thus, the required amount of a therapeutic or a diagnostic biological material is minimized. Due to the immobilization of the therapeutic or diagnostic biological material pharmacokinetic problems caused by circulating active biological material are also minimized.

The method of the invention allows the production of carriers with a clearly defined density of the biological material embedded on the surface of the carrier. Accordingly, the efficiency of the biological material embedded into the matrix of the produced carrier can be clearly and reproducibly defined. Moreover, a therapy which makes use of the carriers produced according to the method of the invention allows a defined onset of a therapy, e.g. by connecting the (medical) device comprising the carrier with the circulation of a body fluid, and a defined termination of the therapy, e.g. by disconnecting the device from the circulation of the body fluid.

A further superior feature of the carrier produced by the method of the invention is the improvement of the stability (shelf life) of the embedded biological material compared to conventionally produced material. Whereas the applicant does not wish to be bound by any theory it is believed that this improvement is achieved by the provision of the coating matrix which reduces the accessible surface of the biological material for degenerative processes. According to this understanding the embedded biological material is protected and supported in its structure by the surrounding coating matrix.

For example is the degradation or decomposition of antibodies coated to the carrier of the invention delayed or inhibited since the second layer applied to the carrier after coating the antibodies is protecting and stabilizing them.

Another superior feature of the method of the present invention and the produced coated carrier is the fact that the coating layer applied to the carrier in step (c) of the method of the invention enables for the sterilization of the produced carrier. Thus, for the first time, the present invention discloses a method of producing a solid coated carrier, coated with an, in general, comparably unstable and labile biological material, which can be sterilized and thus be applied in the treatment of patients or in methods where a sterile environment is needed. The second layer or coating matrix may well prevent the biological material coated to the carrier from degradation due to β-, γ- or X-ray-radiation in addition to enhancing its stability, as discussed above and shown in the appended examples.

In a preferred embodiment of the invention the method further comprises a step (d) after step (c):
(d) drying the carrier until the residual water content is <20% (w/w).

In accordance with this preferred embodiment of the invention the residual water content may be calculated in a manner as known for the determination of the water content of wood. In the case of wood, the percentage of water content of wood (x) is determined by the calculation of the ratio between the mass of the water in the sample ($m_w$) and the mass of the water containing wood sample ($m_u$), multiplied with 100. The mass of a water in the sample ($m_w$) can be determined by subtraction of the mass of the sample after its desiccation from the mass of the water containing wood sample ($m_u$). Accordingly, the percentage of water content of wood is calculated by the following formula:

$$X(\%) = \frac{m_w}{m_u} * 100$$

The residual water content of a preparation of carriers can be determined in analogy, wherein $m_w$ is the mass of the water in the sample of carriers and $m_u$ is the mass of the sample of carriers after the complete desiccation of the sample. In case of a spongiform carrier, $m_w$ is determined after squeezing the excess water out of the pores.

In another preferred embodiment of the invention, the method further comprises a step (a') after step (a):

(a') drying the carrier until the residual content of the solution is less than 10%, preferably less than 5%, more preferably less than 2% such as less than 1%, 0.5% or 0.2% of the originally applied solution. Preferred drying methods are described above. It is most preferred that drying is effected by air-drying.

The method of the invention may further comprise a step (b') subsequent to the step (b) and previous to step (c):

(b') incubating the carrier in a buffered aqueous solution containing a blocking agent and removing the aqueous solution.

A blocking agent may be used in the method for the production of a solid carrier in order to prevent unspecific binding of material added in subsequent steps of the method. This blocking may also have a positive effect on the conformation stability of the biological material before the incubation of the carrier in an aqueous solution according to step (c).

Blocking agents in line with the present invention comprise but are not limited to human or animal serum and proteins of such sera, (e.g. albumin), milk, egg proteins, plant derived proteins (e.g. soya, wheat) including hydrolysates of said proteins (e.g. gelatin, collagen). The buffered aqueous solution containing said blocking agent may also comprise amino acids (preferably glycine, aspartic and/or glutamic acids, proline, arginine, alanine, asparagine, aspartic acid, glutamic acid, glutamine, carnitine, ornithine, hydroxyproline, cysteine, homocysteine, citrulline, inuline, phenylanine, lysine, leucine, isoleucine, histidine, methionine, serine, valine, tyrosine, threonine, tryptophan) or derivates of amino acids (e.g. n-acetyl-tryptophan, beta-alanine, melanin, DOPA), sugars (preferably glucose, saccharose, sucrose), poly alcohols (preferably sorbitol, mannitol, glycerol, xylitol), polyethyleneglycol (PEG), hydroxyethylstarch (HES), phosphates (e.g. sodiummonodihydrogenphosphate, disodiumhydrogenphosphate), amphiphilic substances (preferably detergents like polysorbate, Triton X-100, buffers (preferably TRIS, HEPES).

Preferably the aqueous solution comprising the blocking agent is buffered and of low salt content as defined above. An example for a buffered aqueous solution containing a blocking agent according to the invention is given in the appended examples. The blocking takes preferably place at room temperature for usually 1 to 4 hours, preferably 1 hour.

Alternatively to step (b'), the method of the invention comprises a step (b") to be carried out subsequent to step (b) and previous to step (c):

(b") blocking unbound binding sites using an aqueous solution containing 0.5-10% (w/w) substances selected from the group consisting of (poly)peptides (e.g. albumin, gelatin or collagen), hydroxyethylstarch (HES), mannitol, sorbitol and polyethyleneglycol (PEG), milk, soya, wheat or egg derived protein.

In an even more preferred embodiment step (b') or (b") further comprises performing one or more washing steps using an aqueous solution as defined as suitable for step (b) above after blocking. An aqueous solution suitable in this embodiment is e.g. PBS with 1% human albumin. This one or more washing steps are effected to remove excess blocking agent. The washings are usually effected for 10 seconds to 10 minutes, depending on the surface of the carrier, preferably at room temperature.

In a further preferred embodiment the carrier in step (c) is incubated in an aqueous solution comprising one or more substances selected from the group consisting of albumin, hydroxyethylstarch (HES), mannitol, sorbitol and polyethyleneglycol (PEG).

In line with the invention it is further preferred that the material of the carrier produced by the method of the invention is of porous structure.

To achieve a compact design of the coated carrier to be used as a (medical) product it is preferred that the carrier displays a relatively large surface as compared to its overall measurement. This can be achieved e.g. by using a foam with an open porous structure, a fleece (wadding) or a setting using many parallel small tubes or filaments, for example those similar to a porous hollow fiber design currently used in hemodialysis (see e.g. the World-Wide-Web (www) at fmc-ag.com/internet/fmc/fmcag/agintpub.nsf/Content/Modern_hemodialysis_+the_first_hollow-fiber_dialyzers_2004). The design preferably allows for a free flow of whole blood or the above described other body fluids, and the carrier is preferably rheologically optimized by a minimum pressure difference between the inflow and outflow and a blood flow of <1 m/sec at any point within the device. It is preferably without "dead ends" and optimized for contacts of blood constituents with the active surface of the matrix. The specific advantage of a carrier with porous structure is the increase of the carrier surface to which the biological material can be attached to. Namely, the amount of biological material which can be attached/embedded on a carrier is increased by the increase of the carrier surface per carrier volume.

More preferably, the material of the carrier is characterized by a surface/gaseous volume ratio in a range of 30 $cm^{-1}$ to 300 $cm^{-1}$. The surface of a carrier is understood as the sum of the surfaces of all trabeculae. The gaseous volume is understood as the sum of the volume of gas in all trabeculae of a carrier having a porous structure. The surface/gaseous volume ratio may be e.g. determined by cutting a small piece of foam with a defined overall measurement. All trabeculae of said piece of foam are counted as well as measured microscopically. Using the mean length and diameter of a trabecula as well as the count of the trabeculae per $cm^3$ the specific surface (xx $cm^2/cm^3$, which is $cm^{-1}$ and describes the inner surface of a defined volume of material) can be obtained mathematically (assuming the trabeculae are round in shape).

The material of the carrier with porous structure is preferably characterized by a material volume ratio uncompressed/compressed in a range of 4 to 40.

The term "material volume ratio" is understood in the context of the invention as a ratio between uncompressed and compressed porous material, comprising solid and gaseous components.

In the case of a porous, elastic foam like e.g. PU-foam, the ratio can for example be determined principally as follows. A cylindrical piece of foam with a volume of 20 ml (uncompressed) is placed into a syringe with a volume of 20 ml, and the compressed volume is readable on the marks of the syringe after pressing the plunger fully down. The force that is used for the compression of the material (in the case of PU porous foam) is defined as at least 20 $kg/cm^2$. The endpoint of volume reduction is defined as the volume at which a doubling of the compression pressure (in the case of PU porous foam the pressure will be 40 $kg/cm^2$, respectively) will not result in a further volume reduction of up to 10%. This procedure (doubling of pressure force) may be repeated until the material does not undergo further volume reduction of up to 10%.

In line with the method of the invention it is further preferred that the material of the carrier is selected from the group consisting of glass, polyurethane (PU), polyester, polysulfone, polyethylene, polypropylene, polyacrylic, polyacrylonitrile, polyamide, PMMA, fleece wadding, open porous foam plastic or glass and reticular plastic or glass and structures derived from marine sponges (porifera). For example, a polyester fleece may be used as described for the device LG6 from Pall, Dreieich, Germany. A non-limiting example for glass-filaments includes biofilter membranes for a blood transfusion set with Leukocyte Removal Filter as distributed by Nanjing Shuangwei Science & Technology Industries Co. LTD. Examples for suitable marine sponges are described e.g. in D. Green et al., Tissue Engineering. (2003) Vol. 9, No. 6: 1159-1166.

The material that may be used in the method of the present invention may have the structure of hollow fiber. A hollow fiber package is preferably characterized by a material volume ratio between uncompressed and compressed porous material in a range of 1 to 10 and/or the surface/gaseous volume ratio is in a range of 200 cm$^{-1}$ to 2000 cm$^{-1}$.

In a further preferred embodiment of the method of the invention the solution in step (a) is an aqueous solution. In an alternatively preferred embodiment of the method of the invention the solution in step (a) is a non-aqueous solution. Examples for corresponding solutions and for preferred solutions have been described herein above.

In line with the method of the invention it is preferred that the at least one silane is selected from the group consisting of alkoxysilanes, organofunctional silanes, hydrogensil(ox)anes, siloxanes and organosilanes comprising silyl compounds with other functional groups.

Examples for the recited groups of silanes to be used in the context of the invention comprise:
N-[3-(Trimethoxysilyl)propyl]ethylenediamine,
N-Cyclohexylaminomethylmethyldiethoxysilane
N-Cyclohexylaminomethyltriethoxysilane
N-Phenylaminomethyltrimethoxysilane
(Methacryloxymethyl)methyldimethoxysilane
Methacryloxymethyltrimethoxysilane
(Methacryloxymethyl)methyldiethoxysilane
Methacryloxymethyltriethoxysilane
(Isocyanatomethyl)methyldimethoxysilane
N-Trimethoxysilylmethyl-O-methylcarbamate
N-Dimethoxy(methyl)silylmethyl-O-methyl-carbamate
N-Cyclohexyl-3-aminopropyltrimethoxysilane
3-Aminopropyltriethoxysilane
N-(2-Aminoethyl)-3-aminopropylmethyldimethoxysilane
3-Aminopropyltrimethoxysilane
3-Methacryloxypropyltrimethoxysilane
3-Methacryloxypropyltriacetoxysilane
3-Isocyanatopropyltrimethoxysilane
3-Glycidoxypropyltrimethoxysilane
3-Glycidoxypropyltriethoxysilane
3-(Triethoxysilyl)propylbernsteinsäureanhydride
3-Aminopropyl)tris[2-(2-methoxyethoxy)ethoxy]silane
(3-Aminopropyl)tris(trimethylsiloxy)silane
(4-Methoxyphenyl)tri(O-tolyl)silane
(4-Phenoxyphenyl)(phenyl)(O-tolyl)silane
Dicyclohexyl-methyl-silane
Dimethyl(3-phenylpropyl)silane
Dimethylbis(2,3,4,5-tetramethyl-2,4-cyclopentadien-1-yl) silane
Diphenyl(3-Phenylpropyl)silane
Diphenyl(4-Methoxyphenyl)silane
Diphenyl(4-Phenoxyphenyl)silane
Diphenyl(diphenylmethoxy)(diphenylmethyl)silane
Diphenyl(diphenylmethyl)silane
Diphenyl(M-tolyl)silane
Diphenyl(O-tolyl)(4-Trimethylsilyl)phenyl)silane
Diphenyl(P-tolyl)silane
Diphenyldi(M-tolyl)silane
Diphenyldi(O-tolyl)silane
Diphenylmethyl(O-tolyl)silane
Diphenylphenethyl(O-tolyl)silane
Dodecyltris(2-Biphenylyl)silane
Dodecyltris(2-Cyclohexylethyl)silane
Dodecyltris (3-Fluorophenyl) silane
Dodecyltris (M-tolyl) silane
Ethoxytri(O-tolyl) silane
Ethoxytris(2-Methoxyphenyl)silane (1)
Ethyl-bis-(2,4,6-trimethyl-phenyl)-silane (1)
Ethylenebis(tris(decyl)silane) (1)
Hexadecylsulfanylethynyl-trimethyl-silane
Isobutyl(trimethoxy)silane (2)
Methyl-tris(trimethylsiloxy)silane (1)
Methylphenyl(4-(Trimethylsilylmethyl)phenyl)silane (1)
Methylphenyl(M-tolyl)silane (1)
Methyltris(2-Methoxyethoxy)silane
Phenyl(O-tolyl)silane (1)
Phenyl-tris(trimethylsiloxy)silane (1)
Phenyltri(M-tolyl)silane (1)
Phenyltri(O-tolyl)silane (1)
Phenyltri(P-tolyl)silane
Phenyltris(2-Cyclohexylethyl)silane
Phenyltris(2-Ethylhexyl)silane
Phenyltris(2-Methoxyethoxy)silane
Phenyltris(4-(Trimethylsilyl)phenyl)silane
Phenyltris(9-ethyl-3-carbazolyl)silane
Tri(O-tolyl)silane
Triacetoxy(ethyl)silane
Triacetoxy(methyl)silane
Triacetoxy(vinyl)silane
Triethoxy(1-phenylethenyl)silane
Triethoxy(3-isocyanatopropyl)silane
Triethoxy(3-thiocyanatopropyl)silane
Triethoxy(4-methoxyphenyl)silane
Triethoxy[4-(trifluoromethyl)phenyl]silane
Triethoxy(ethyl)silane
Triethoxy(isobutyl)silane
Triethoxy(octyl)silane
Triethyl(silane-d)
Trihexadecyl(4-(Trimethylsilyl)phenyl)silane
Trimethoxy[2-(7-oxabicyclo[4.1.0]hept-3-yl)ethyl]silane
Trimethoxy(2-phenylethyl)silane
Trimethoxy[3-(methylamino)propyl]silane
Trimethoxy[3-(phenylamino)propyl]silane
Trimethoxy(7-Octen-1-yl)silane
Trimethoxy(octadecyl)silane
Trimethoxy(octyl)silane
Trimethoxy(propyl)silane
Trimethoxy(vinyl)silane
Trimethyl(1,2,3,4,5-pentamethyl-2,4-cyclopentadien-1-yl) silane
Trimethyl-(1-methyl-1-phenyl-propoxy)-silane
Trimethyl(1-Propenyl) silane
Trimethyl(2,3,4,5-tetramethyl-2,4-cyclopentadien-1-yl)silane
Trimethyl(2-Phenyl-1,1-bis(trimethylsilyl)ethyl)silane
Trimethyl-(4'-Naphtalen-1-yl-biphenyl-4-yl)-silane Trimethyl-(4-Nitro-phenylethynyl)-silane
Trimethyl(4-(Trimethylsilyl)butoxy)silane
Trimethyl(methylthio)silane
Trimethyl(phenoxy)silane
Trimethyl(phenyl)silane
Trimethyl(phenylselenomethyl)silane
Trimethyl(phenylthio)silane
Trimethyl(phenylthiomethyl)silane
Trimethyl(propargyl)silane
Trimethyl(propoxy)silane
Trimethyl(vinyl)silane
Triphenyl(1,2,2-triphenylethyl)silane
Triphenyl(3-(Triphenylgermyl)propyl)silane
Triphenyl(triphenylmethyl)silane
Triphenyl(vinyl)silane
Tris(1-Naphtyl)silane
Tris(2-Biphenyl)silane
Tris(4-(Trimethylsilyl)phenyl)silane
Tris(decyl)silane
Tris(hexadecyl)silane
Tris(isopropylthio)silane
Tris(phenethyl)silane
Tris(trimethylsiloxy)silane
Tris(trimethylsilyl)silane
Triethylsilane
1-(Dimethylsilyl)-2-phenylacetylene
3-(Triethoxysilyl)propyl isocyanate
3-(Trimethoxysilyl)propyl methacrylate
3-[Tris(trimethylsiloxy)silyl]propyl methacrylate
Allyl(4-methoxyphenyl)dimethylsilane
Dimethoxy-methyl-octadecylsilane
Methoxypolyethylene glycol 5,000 trimethylsilyl ether
N-[3-(Trimethoxysilyl)propyl]aniline
Propargyltrimethylsilane
Silicon 2,3-naphthalocyanine bis(trihexylsilyloxide
tert-Butyldimethylsilyl trifluoromethanesulfonate
Tetraallyl orthosilicate
Tetraallylsilane
Tetrakis(dimethylsilyl) orthosilicate
Tetramethyl-d12 orthosilicate
Trimethylsilyl trifluoromethanesulfonate
Tris(dimethylsiloxy)phenylsilane
Vinyltrimethoxysilane
Vinyltrimethylsilane
Vinyltrimethylsilane
3-(2-Aminoethylamino)propyl-dimethoxymethylsilane
[3-(2-Aminoethylamino)propyl]trimethoxysilane
Allyltrimethylsilane and
Methyl 2-(trimethylsilyl)propionate In accordance with the method of the invention it is additionally preferred that the biological material is selected from the group consisting of eukaryotic cells, fragments of eukaryotic cells, prokaryotes, fragments of prokaryotes, archaebacteria, fragments of archaebacteria, viruses and viral fragments. The recited fragments of eukaryotic cells, prokaryotes, archaebacteria and viruses comprise (poly) peptides, oligonucleotides, polynucleotides, polysaccharides and combinations thereof.

The group of eukaryotic cells includes yeast cells, cells of lower and higher plants, insect cells as well as cells of higher animals. Preferably, said cells of higher animals are mammalian cells, more preferably human cells.

Fragments of eukaryotic cells, prokaryotes and archaebacteria are understood in accordance with the invention to comprise preparations of membrane fractions (membrane vesicles) or of cellular compartments such as nucleoli or organelles from eukaryotic cells or constituents of the bacterial cell wall such as lipopolysaccharides (LPS), peptidoglycans and lipotechoic acids. The group of fragments of eukaryotic cells, prokaryotes and archaebacteria may also comprise (poly)peptides such as antigenic proteins such as fimbriae, proteases, heat-shock proteins, formyl-methionyl peptides, and toxins, Toll-like receptors (TLRs), nucleotide-binding oligomerization domain proteins (Nod) and G-protein-coupled receptors, formyl-methionyl peptide receptors, protease-activated receptors and glycoproteins. The group of glycoproteins includes immunoreceptors and ligands. The immunoreceptors and ligands comprise MHC complexes (loaded with antigenic peptides or MHC molecules alone) and co-stimulatory molecules.

Examples for fragments of viruses comprise but are not limited according to the invention to molecules such as polypeptides of the outer membrane of a virus (e.g. envelope proteins) which are important for the interaction and fusion with host cell membranes. Further examples for fragments of viruses also comprise core viral proteins and fragments thereof.

In an alternative embodiment of the method of the invention the biological material is selected from the group consisting of (poly)peptides, oligonucleotides, polynucleotides and polysaccharides which are produced synthetically or semisynthetically or recombinantly. By this alternative definition of the biological material used in the method of the invention (poly)peptides, oligonucleotides, polynucleotides and polysaccharides are comprised which lack a counterpart in nature as well as chemically modified derivatives of naturally occurring as well as artificial (poly) peptides, oligonucleotides, polynucleotides and polysaccharides. Methods for the synthetic or semisynthetic or recombinant production of poly)peptides, oligonucleotides, polynucleotides and polysaccharides are known in the art.

In accordance with the invention it is particularly preferred that the (poly)peptide is a receptor. Examples for corresponding receptors comprise membrane bound and intracellular receptors as well as soluble receptors. A particularly preferred embodiment of such a receptor is an antibody. Receptors in the context of the invention are understood to specifically interact with a ligand (counterpart of the receptor; in the case of an antibody an antigen). Interaction of a functional receptor (preferably a signal transducing receptor in contrast to non-transducing or truncated receptors) with its ligand may result in the initiation of a signal cascade. Examples for such functional receptors comprise the T cell receptor (TCR) and B cell receptor (BCR) or costimulatory receptors (e.g. CD28) which are involved in the activation of cells of the immune system. Interaction of a functional receptor with its ligand may also result in the initiation of different cellular signals such as apoptosis e.g. via Fas (CD95) or other receptors of the TNF-superfamily including the TNF-α receptor family, TRAIL, Death Receptors, Toll like receptors and $F_c$-receptors. Moreover, in line with the invention the interaction of a functional receptor with its ligand may also result in the initiation of inhibitory signals such as signals via CTLA-4.

As has been stated above, it is further preferred that said receptor is an antibody, an antibody fragment or a derivative of an antibody.

The antibodies described in the context of the invention are capable to specifically bind/interact with an epitope. The epitope may be a polypeptide structure as well as compounds which do not comprise amino acids. The term "specifically binding/interacting with" as used in accordance with the present invention means that the antibody or antibody fragment does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest. Corresponding methods are described e.g. in Harlow and Lane, Antibodies: A Laboratory Manual, Cold Spring Harbor Laboratory Press, 1988 or Harlow and Lane, Using Antibodies: A Laboratory Manual, Cold Spring Harbor Laboratory Press, 1999)

The antibody or antibody fragment or antibody derivative specifically binds to/interacts with conformational or continuous epitopes of an antigen. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela, (1969) Science 166, 1365 and Laver, (1990) Cell 61, 553-6). The two or more discrete amino acid residues contributing to the epitope are present on separate sections of one or more (poly)peptide chain(s). These residues come together on the surface of the molecule when the (poly)peptide chain(s) fold(s) into a three-dimensional structure to constitute the epitope. In contrast, a linear or continuous epitope consist of two or more discrete amino acid residues which are present in a single linear segment of a (poly)peptide chain.

The antibody may be a monoclonal or a polyclonal antibody of any class of antibody. The term "antibody" also comprises derivatives or fragments thereof which still retain the binding specificity. The antibody of the invention also includes embodiments such as synthetic, chimeric, single chain and humanized antibodies, as well as antibody fragments.

The term "antibody fragment" relates to fragments, such as Fab, F(ab$_2$)' or Fv fragments. The term "antibody derivative" defines in the context of the invention chemically modified antibodies and antibody fragments. This includes scFv fragments, single domain antibodies etc. Accordingly, antibody derivatives are often (poly)peptides derived from antibody molecules and/or (poly)peptides which are modified by chemical/biochemical or molecular biological methods. The minimal requirement for the specific interaction of an antibody fragment with its specific antigen is the presence of one or more CDRs from the variable heavy chain ($V_H$) and the variable light variable chain ($V_L$) of the parent antibody in a context which allows for the fitting of the antibody fragment and the epitope. Such a context can be provided by the use of a suitable framework of an antibody. As known in the art the term "framework" defines in the context of an antibody or antibody derivative the amino acid sequence which functions as a spacer between the CDRs as well as extends N-terminally and C-terminally thereof and provides for a structure which allows the formation of the antigen binding site by the CDRs. A modification of the framework or CDR sequences, e.g. to improve the binding affinity by molecular biological methods may comprise modification of the (poly)peptides using conventional techniques known in the art, for example, by using amino acid deletion(s), insertion(s), substitution(s), addition(s), and/or recombination(s) and/or any other modification(s) (e.g. post-translational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook et al., Molecular Cloning: A Laboratory Manual, Cold Spring Harbor Laboratory Press, 2nd edition 1989 and 3rd edition 2001; Gerhardt et al., Methods for General and Molecular Bacteriology, ASM Press, 1994; Lefkovits, Immunology Methods Manual: The Comprehensive Sourcebook of Techniques, Academic Press, 1997; or Golemis, Protein-Protein Interactions: A Molecular Cloning Manual, Cold Spring Harbor Laboratory Press, 2002.

As noted herein above, it is further preferred that the antibody is a monoclonal antibody.

It is most preferred that the (monoclonal) antibody is of the IgG, IgM or IgY class.

In line with a further preferred embodiment of the method of the invention the biological material attached in step (b) is covalently bound to said carrier. Methods, how to achieve an attachment of the biological material to the carrier via a covalent bond have been described herein above.

In line with a further preferred embodiment of the method of the invention the steps (a) to (c) are effected in a system of rotating tubes that contain the carrier.

Moreover, in line with a further preferred embodiment of the method of the invention the solutions are rotated in the system of tubes via a pump.

In a different particularly preferred embodiment of the method of the invention the carrier made of a material having a porous structure comprises at least one further material. For example, in case the carrier of the invention is made of one of the materials as defined above providing one or more chemical entities, on or more other materials can be added to provide different chemical entities or to alter the properties of the carrier. The same holds true in case the carrier is made of two, three or more materials. In other terms, besides the substances defined above, the carrier used for coating according to the present invention comprises at least one further material. The material can be worked into the carrier upon its production by mixing the ingredients or by filling the carrier with the one or more additional materials. Preferably, said at least one further material is selected from the group consisting of carbon, $SiO_2$, hydroxyethylstarch (HES) and biotin. Examples for a porous carrier comprising one further material include e.g. carbon filled polyurethane and polyether foam from Kinetic Concepts Inc. (KCI, Texas, USA).

In line with a further preferred embodiment of the method of the invention the solution in steps (a) to (c) is an aqueous solution which comprises 0.5 to 10% albumin (v/v) and 0.5 to 5% mannitol (v/v). It is particularly preferred in accordance with the invention that the aqueous solution in steps (a) to (c) comprises 0.6 to 3% albumin (v/v). The aqueous solution preferably comprises 0.6 to 3% of a sugar (e.g. mannitol) (v/v).

In one alternative embodiment, the solution in step (a) is an alcohol with silane 0.1-10% (v/v), the one in step (b) is an aqueous solution which comprises the biological material (for example antibodies) and (c) is an aqueous solution which comprises 0.5 to 10% albumin (v/v) and 0.5 to 5% mannitol (v/v). It is particularly preferred in accordance with the invention that the aqueous solution in steps (a) to (c) comprises 0.6 to 3% albumin (v/v). The aqueous solution preferably comprises 0.6 to 3% of a sugar (e.g. mannitol) (v/v).

The method of the invention may further comprise a step (e) of sterilizing the solid coated carrier. The ability to sterilize the solid coated carrier produced by the method of the invention allows, inter alia, the production of the solid coated carriers under non-sterile or semi-sterile conditions, wherein the so produced carriers may still be used in the method of the invention which involves the contact of the solid coated carrier with a body liquid in vivo or ex vivo. This represents a further superior feature of the method and the so produced carrier of the invention since, due to that feature, the costs for the production of the solid carrier can be reduced compared to costs for the production of carriers which may not be sterilized. This is because, in the production process, sterile conditions are not required. As it is well known, conventionally prepared carriers are not suitable for a sterilization and must be produced under completely sterile conditions. Moreover, a cost contributing feature is that said carriers may be recycled after their use by sterilization. The recycled carriers may subsequently be used in a further treatment of the same or a different patient or in a further or the same method for diagnosing which again involves the contact of the carrier with a body liquid in vivo or ex vivo.

Preferably, the sterilization or recycling of the carrier is effected by ethyleneoxide (EO), beta radiation, gamma radiation, X-ray, heat inactivation, autoclaving or plasma sterilization depending on the carrier material. It is most preferred that the carrier is sterilized by β- or γ-radiation. Suitable in this embodiment is β-radiation with a dose of 25 kgray using an electron accelerator with 10 MeV. To a certain extent sterilization with ethyleneoxide can be applied to the carrier of the invention. In general, the method of sterilization has to be chosen in order not to harm the desired activity of the coated biological material. This can be effected with fragments of cells, (poly)peptides, especially antibodies or receptors, polynucleotides or polysaccharides or complexes thereof as defined above. For cells of any kind, suitable means of sterilization are not known to date. Thus, embodiments where living cells are used as the biological material and the carrier is sterilized are not part of this invention.

In a further embodiment the present invention provides a solid coated carrier producible or produced by the method of the invention.

In a further alternative embodiment the present invention provides a solid coated carrier to which biological material is attached, wherein the biological material is embedded into a coating matrix consisting of a first layer of at least one silane which is in direct contact with the carrier and a second layer covering the first layer consisting of at least one substance selected from the group consisting of at least one (poly)peptide, at least one amino acid, starch, at least one sugar, at least one phosphate, at least one polyalcohol and polyethyleneglycol (PEG) or a mixture thereof. More preferred, the at least one substance of the second layer is selected from the group comprising inter alia human or animal serum and proteins of such sera, (e.g. albumin), milk, egg proteins, plant derived proteins (e.g. soya, wheat) including hydrolysates of said proteins (e.g. gelatin, collagen), the group of amino acids (preferably glycine, aspartic and/or glutamic acids, proline, arginine, alanine, asparagine, aspartic acid, glutamic acid, glutamine, carnitine, ornithine, hydroxyproline, cysteine, homocysteine, citrulline, inuline, phenylanine, lysine, leucine, isoleucine, histidine, methionine, serine, valine, tyrosine, threonine, tryptophan) or derivates of amino acids (e.g. n-acetyl-tryptophan, beta-alanine, melanin, DOPA), the group of sugars (preferably glucose, saccharose, sucrose), poly alcohols (preferably sorbitol, mannitol, glycerol, xylitol), polyethyleneglycol (PEG), hydroxyethylstarch (HES), the group of phosphates (e.g. sodiummonodihydrogenphosphate, disodiumhydrogenphosphate) or a mixture thereof.

It is preferred that the solid coated carrier is produced in accordance with the method of the invention.

Definitions and explanations inter alia of the carrier, the biological material, the attachment of the biological material and the material of the coating matrix provided in accordance with the method of the invention mutatis mutandis apply to the solid coated carrier of the invention.

Also, the particular superior features of the solid coated carrier of the present invention have been described herein above in the context of the characterization of the method of the invention.

As also described in the context of the method of producing a solid coated carrier of the invention it is also preferred that the material of the carrier is selected from the group consisting of glass, polyurethane, polyester, polysulfone, polyethylene, polypropylene, polyacrylic, polyacrylnitrile, polyamide, PMMA, fleece wadding, open porous foam plastic, reticular plastic and structures derived from marine sponges (porifera).

According to a preferred embodiment of the solid coated carrier of the invention the biological material is selected from the group consisting of eukaryotic cells, fragments of eukaryotic cells, prokaryotes, fragments of prokaryotes, archaebacteria, fragments of archaebacteria, viruses and viral fragments. Preferably, the fragments of eukaryotic cells, fragments of prokaryotes, fragments of archaebacteria, or viral fragments are selected from the group consisting of (poly)peptides, oligonucleotides, polynucleotides and polysaccharides.

In an alternative embodiment of the solid coated carrier of the invention the biological material is selected from the group consisting of (poly)peptides, oligonucleotides, polynucleotides and polysaccharides which are produced synthetically or semisynthetically or recombinantly.

In an also preferred embodiment of the carrier of the invention the at least one (poly)peptide of the second layer is albumin, the starch of the second layer is hydroxyethylstarch (HES) and/or the at least one sugar of the second layer is mannitol or sorbitol.

It is preferred that the material of a carrier having a porous structure is characterized by an surface/gaseous volume ratio in a range of 30 $cm^{-1}$ to 300 $cm^{-1}$.

It is also preferred that the material of the carrier having a porous structure is characterized by a material volume ratio uncompressed/compressed in a range of 4 to 40.

In a further preferred embodiment the material of the carrier is hollow fiber. A hollow fiber package is preferably characterized by a material volume ratio uncompressed/compressed in a range of 1 to 10 and/or the surface/gaseous volume ratio is in a range of 200 $cm^{-1}$ to 2000 $cm^{-1}$.

It is additionally preferred that the at least one silane of the first layer is selected from the group consisting of alkoxysilanes, organofunctional silanes, hydrogensil(ox)anes, siloxanes, organosilanes comprising silyl compounds with other functional groups. Examples of appropriate silanes have been provided above.

In line with the invention the second layer of the carrier may be a preferably dried mixture comprising albumin and mannitol. Preferably, said mixture further comprises polyethyleneglycol (PEG). In particular, in accordance with the present invention, the mixture is applied to the carrier in liquid form and subsequently dried on the surface of the carrier of the invention. Drying is preferably effected by air-drying.

In a further preferred embodiment of the invention the biological material is covalently bound to said carrier. Methods to achieve a covalent binding of biological material to a solid carrier are described herein above and in the appended example 2.

It is further preferred for the solid coated carrier of the invention that the (poly)peptide in item (b), which is embedded in the coating matrix, is a receptor. More preferably, said receptor is an antibody or an antibody fragment. It is particularly envisaged according to a further preferred embodiment of the invention that the antibody is a monoclonal antibody.

The (monoclonal) antibody embedded into the coating matrix of the carrier of the invention may be an antibody of any class of antibody. Preferably, the antibody is of the IgG, IgY or IgM class.

It is particularly preferred that the carrier of the invention comprises at least one further material. For example, in case the carrier of the invention is made of one of the materials as defined above providing one or more chemical entities, on or more other materials can be added to provide different chemical entities or to alter the properties of the carrier. The same holds true in case the carrier is made of two, three or more materials. In other terms, besides the substances defined above, the carrier used for coating according to the present invention comprises at least one further material. The material can be worked into the carrier upon its production by mixing the ingredients or by filling the carrier with the one or more additional materials. Preferably, said at least one further material is selected from the group consisting of carbon, $SiO_2$, HES and biotin.

In another preferred embodiment of the present invention the carrier is sterilized by β- or γ-radiation. Suitable in this embodiment is β-radiation with a dose of 25 kgray using an electron accelerator with 10 MeV.

In a further alternative embodiment the present invention provides the use of a solid coated carrier according to the invention for the preparation of a (medical) device for the contacting, filtering or cleaning of blood, lymph or liquor cerebrospinal of a patient. The term "(medical) device" defines in the context of the invention a device which comprises a solid coated carrier according to the invention or produced by a method of the invention. Examples of such devices are exemplified herein below. The device is suitable to enable a contacting, filtering or cleaning of blood, lymph or liquor cerebrospinal of a patient e.g. by connecting the device with the circulation of the body fluid of the patient and thereby treating a patient as described herein above (in the context of the method for the production of the solid coated carrier). Moreover, the (medical) device may be suitable for the qualitative or quantitative detection of compounds as well as trapping certain cells, e. g. stem cells, in a sample of a body fluid of a patient as also described in part herein above. Stem cells comprise pluripotent, multipotent or totipotent stem cells. By trapping certain cells or one or more cell populations with the carrier of the invention suitably coated with one or more biological materials as defined above which are specifically binding to these cells or cell populations(s) by contacting in a sample of a body fluid, at least a part of these cells or cell population(s) can be removed from the sample. In general, different cell lines, cell species or developmental stages of cells can be distinguished by the presence of different antigens on the cell surface. This enables for selective trapping of the desired cells by coating the carrier of the invention with e.g. a corresponding receptor for the antigen or an antibody directed against the antigen.

The term "contacting, filtering or cleaning" as used throughout the present application refers to alternative means of removing one or more compounds from a solution. Accordingly, the term "contacting" may be an initial step of filtering and cleaning.

The disclosed preferably medical device is useful in therapies which comprise the detoxification of body fluids from toxins such as dioxin, botulism toxin, tetanus toxin, LPS, septic poisons etc. Moreover, it is useful in the treatment of bacterial or viral diseases, especially of diseases with a major virus load in the blood or other body fluids (e.g. haemorrhagic fevers, hepatitis a, b, c, d, e, HIV, dengue fever) or a major bacterial load in the blood or alternative body fluids (e.g. sepsis with meningo- or pneumococcal bacteria). A further envisaged alternative application of the disclosed medical device is the use in a therapy which requires the stimulation or elimination of certain cells of a patient. An elimination of a specific population of cells is e.g. indicated in the treatment of proliferative diseases (e.g. minimal residual cancer), autoimmune diseases or a treatment of diseases caused by organ transplantation. A stimulation of a specific population of cells is e.g. indicated in the treatment of a disease which is cured or alleviated by the activation of cells immune system. The population of activated cells is suitable to eliminate a specific population of diseased cells.

Further, the trapping of stem cells using appropriate antibodies affixed to the solid carrier (for example anti-CD34 or CD133 is a useful application of the device. After trapping, the cells are harvested by enzymatic release, cold fluids, mechanical force (vibration etc.) or a combination of these techniques.

Figure 3:
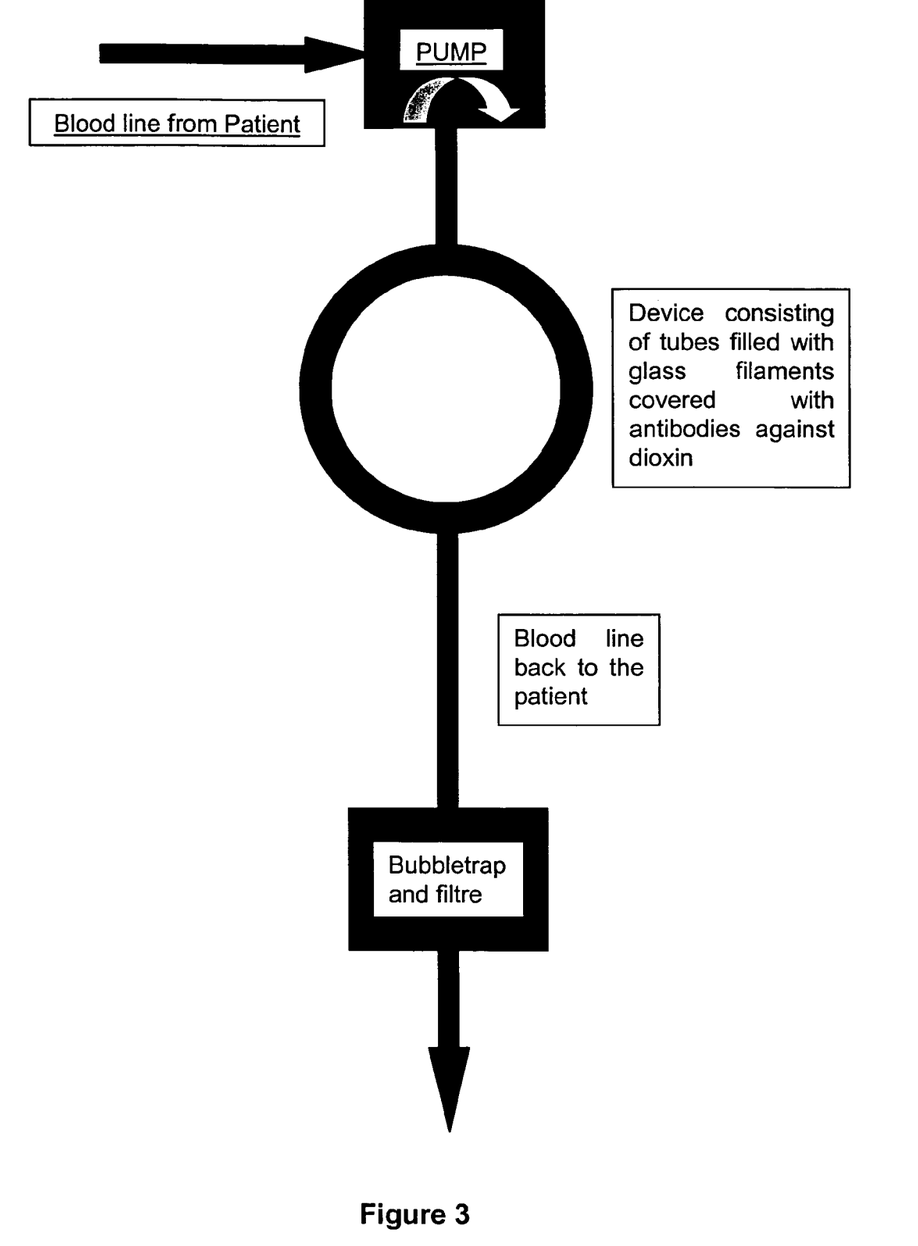
Figure 4:
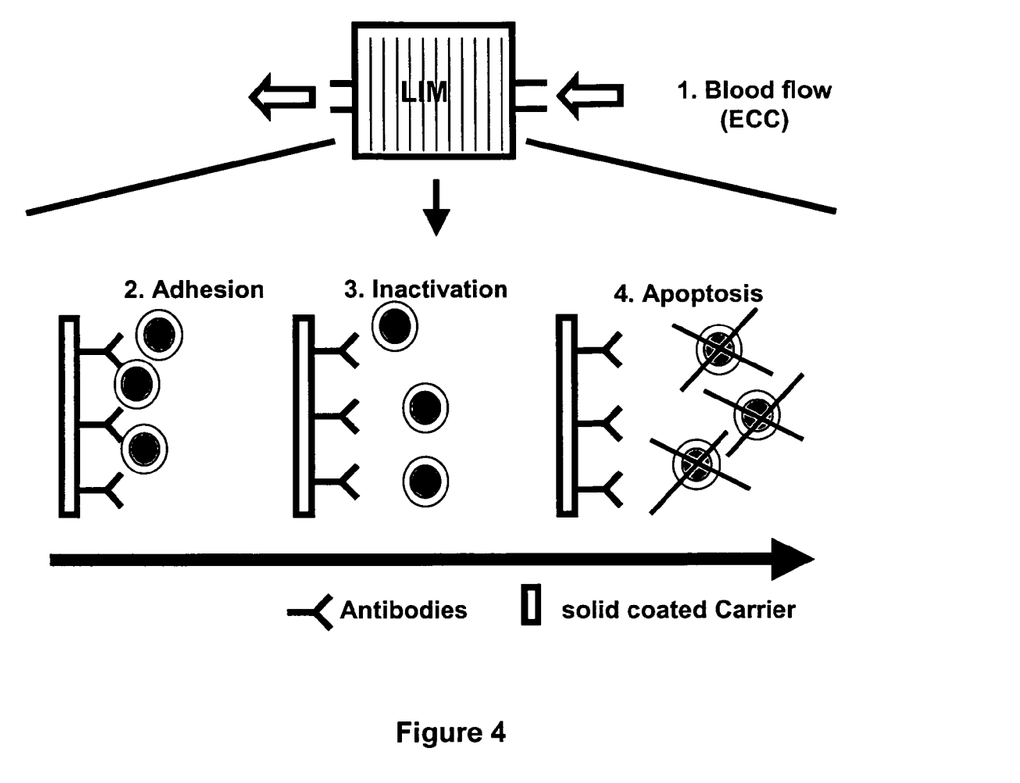

Examples for embodiments of the disclosed (medical) devices are schematically depicted in FIGS. 3 and 4.

One embodiment of the (medical) device includes transient or permanent implants characterized by a surface which itself is a solid coated carrier or to which solid coated carriers according to the invention or produced according to the method of the invention are attached to. This includes osteosynthesis devices, materials used for reconstructive surgery etc. as well as a novel class of stents. Such novel class of stents may have immune catalyzing features (stimulatory, inhibitory or eliminating features as described above).

Further embodiments of the (medical) device include catheters, circuits, devices that are incorporated into the extracorporeal systems, e.g. arterial filters, oxygenators, reservoirs, the Leukocyte Inhibition Module (LIM), Leukocyte Stimulation Module (LSM), Tolerance Induction Module or artificial lymph nodes which comprise solid coated carriers or to which solid coated carriers according to the invention or produced according to the method of the invention are attached to. Such modules have been described e.g. by Scholz M et al. ASAIO J 2005, 51:144-7, Scholz M, Cinatl J Med Res Rev 2005; 25:331-42; Scholz M et al. J Thorac Cardiovasc Surg 2004; 127:1735-42; Moreno J B et al. Perfusion 2004; 19:11-6.

Moreover, further alternative embodiments of the (medical) device are devices which interior walls are solid coated carriers or to which solid coated carriers are attached to including ex vivo vaccination container, apheresis devices, stem cell isolation devices, purging devices, syringes and devices for transient or permanent blood storage (e.g. in blood banks, but also laboratory equipment in routine or research laboratories). An example for a diagnostic (medical) device is an ELISA plate wherein the surface of the plate (or at least of the reaction wells) is a solid coated carrier or solid coated carriers are attached to.

Examples for the above indicated diseases comprise severe hyperlipidemia of variuos origin, homozygous familial hypercholesterolemia, heterozygous familial hypercholesterolemia, defective Apo B-100, isolated Lipoprotein (a) elevation, systemic lupus erythematosus (SLE), Sjögren's syndrome, mixed connective tissue disease, dilated cardiomyopathy (DCM), diseases associated with inhibitors to coagulation factors, idiopathic thrombocytopenic purpura (ITP), thrombotic thrombocytopenic purpura (TTP), autoimmune hemolytic anemia, hyperviscosity syndrome in hypergammaglobulinemia, myasthenia gravis, Guillain-Barré syndrome, chronic inflammatory demyelinating polyneuropathy (CIDP), dysproteinemic polyneuropathies, bone marrow transplantation, endocrine orbitopathy, diabetes mellitus type I (IDDM), Goodpasture's syndrome, nephropathies due to immunoglobulin or immune complex deposits, cryoglobulinemia, pemphigus, atopic dermatitis, graft-versus-host (GvH) diseases, host-versus-graft (HvG) diseases, and various forms of vasculitis.

The invention also provides a method for the manipulation of the composition of blood, lymph or liquor cerebrospinal of a patient comprising the contacting of the blood, lymph or liquor cerebrospinal with a solid coated carrier according to the present invention.

The term "manipulation of the composition" of a body liquid defines a process of affecting the characteristic features of the body liquid or a sample of a different body liquid. This comprises a filtration or cleaning of the liquid. In such a case, biological material, e.g. (a) receptor(s), on the carrier will bind to component(s) of the body fluid and retain said component(s). This step is preferably effected under physiological conditions as defined above. Also comprised by this definition is the induction of a change of the activation status of cells comprised in the sample as well as the elimination of one or more specific populations of cells.

The manipulation of the composition of blood, lymph or liquor cerebrospinal of a patient may be effected in accordance with the invention in vivo, ex vivo or in vitro. In a subsequent step of the ex vivo or in vitro embodiment of the method for the manipulation of the composition of blood, lymph or liquor cerebrospinal of a patient, the blood, lymph or the liquor is removed from the carrier after the contacting with the solid coated carrier.

The contacting of the carrier comprising the embedded biological material in the embodiment where the biological material is a cell, e.g. donor or genetically engineered/recombinant cell, enables the secretion of substances produced by the embedded cell into the body fluid of a patient. The secreted substance is the effective substance in the treatment of a disease of a patient. Diseases that can treated by such an approach comprise e.g. diabetes mellitus (use of islet cells or other cells secreting insulin), endocrinal diseases (e.g. use of cells from the thyroid gland or the pineal body or other cells secreting a hormone helpful in the treatment of a disease). Thus, the method for the manipulation of the composition of blood, lymph or liquor cerebrospinal of a patient described herein enables a treatment of a patient with a minimized risk of a side effect. This is because the donor or genetically engineered/recombinant cells if applied in an in vitro/ex vivo scenario, will not enter the patient. Even if applied in vivo, which, as mentioned, also forms an embodiment in accordance with the invention, these cells will not be released into the blood stream or other body fluids due to the described mode of attachment to the solid carrier.

Preferably, the above described use and the method of the invention are characterized by a manipulation of the composition of blood, lymph or liquor cerebrospinal, which is effected in a batch container which contains the solid coated carrier. Alternatively, the manipulation of the composition of blood, lymph or liquor cerebrospinal is effected in a flow through container which contains the solid coated carrier.

In a further embodiment the invention provides a method for the diagnosis of a disease. The method comprising the steps of:

(a) contacting body liquid of a patient with a solid coated carrier according to the invention into which a receptor is embedded under suitable conditions for a specific binding of a pathogen or marker protein indicative for the disease to the embedded receptor; and (b) detecting whether the pathogen or marker protein indicative for the disease has been bound to the embedded receptor.

The described method may be carried out in vivo, ex vivo or in vitro. Preferably, the receptor is an antibody or a fragment or derivative thereof. Most preferably, the antibody is a monoclonal antibody.

The term "solid coated carrier according to the invention into which a receptor is embedded" means, in accordance with the invention a solid coated carrier producible or produced according to the method of the invention, wherein the biological material in step (b) of the method constitutes or comprises said receptor.

Examples for diseases to be diagnosed with the diagnostic method of the invention comprise the diseases described herein above in the context of the medical use and the method of treatment of the invention. The recited pathogen or marker protein may e.g. be detected by the use of antibodies like anti-p24 (HIV) (see e.g. Schupbach et al. J Aquir Immune Defic Syndr 2005; 40:250-6.) or anti-gB (HCMV) (see e.g. Just-Nubling G et al. Infection 2003; 31:318-23).

Suitable conditions for a specific binding of a pathogen or marker protein indicative of the disease to the attached antibody may be achieved by contacting a sample of the body liquid of the patient with antibody covered surfaces according to the invention under physiological conditions.

The diagnostic method of the invention may comprise the step of incubating the material of a sample of the body liquid under cell culture conditions in order to enrich a pathogen such as a virus, bacterium or a single cell eukaryotic pathogen.

Moreover, the invention provides a diagnostic composition comprising a solid coated carrier according to the invention. The diagnostic composition of the invention will preferably be used for the diagnosis of a disease.

Examples for diseases to be diagnosed with the diagnostic composition of the invention have been described herein above.

In addition, the present invention provides for a method of purifying a compound comprising contacting a mixture comprising the compound to be purified with the solid coated carrier according to the present invention. Depending on the molecule attached or coated to the carrier and specifically binding to a compound, the method of the present invention can be applied to purify e.g. proteins, nucleic acids, protein complexes or other molecules of biological or inorganic origin.

The method of the invention is also suitable to separate proteins of the same kind having different phosphorylation states or having different post-translational modifications using the coated carrier of the invention, wherein the molecule coated to the carrier specifically recognizes one of these states or modifications.

The principle of the method of the present inventions corresponds to that of affinity purification which is commonly known in the art. The person skilled in the art appreciates that different formats can be used to carry out the method of the present invention. For example, commonly applied formats are columns packed with the affinity material, i.e. the coated carrier of the invention.

In a preferred embodiment of the method of the present invention, the molecule attached to the carrier is an antibody as e.g. described above.

The examples illustrate the invention.

Example 1: Induction of Apoptosis in a Cell Population Using the Solid Coated Carrier of the Invention The goal of the experimental approach was to determine the protective effect of the coating procedure in terms of functional activity of immobilized anti-Fas (CD95, APO-1) IgM-antibodies after sterilization with ethyleneoxide or beta-radiation.

Coating of NUNC 8-Well Chamber Slides and Immobilization of Anti-Fas IgM:

Two 8-well chamber slides were used for coating. Each well was treated with 250 µl methanol with 4% (2-5%)N-[3-(Trimethoxysilyl)propyl]ethylenediamine for 30 min at room temperature. After inverse centrifugation and 10 min drying under laminar flow, part of the wells were incubated with 200 µl antibody containing buffer (1:100 represents 1 µg antibody per well on 0.64 cm$^2$) for 1 h at 37° C. and 90% humidity. Untreated wells served as controls. Subsequently, wells were treated with a blocking solution (PBS with 5% serum and 5% mannitol) for 30 min., washed three times with the blocking solution and dried as described above. The coated wells can be stored at 4° C. for several weeks. Sterilization was carried out at 1.7 bar, 45° C., 180 min 6% EO, 94% CO2, with a maximum temperature of 47° C.

Assay with Jurkat Cells:

Three to five days after splitting, 1×10$^5$ Jurkat cells were added to each of the the prepared wells (according to the description above) in the presence of 2% serum and incubated overnight. After 48 h, 8 µl propidium iodide (PI) and 1 µl annexin V were added to each well. Apoptotic cells bind annexin V and necrotic cells take up PI. After 15 min cells were gently removed from the wells and the fluorescence determined by flow cytometry (apoptosis: FL1; necrosis: FL2).

Wells were washed carefully with PBS and stored at 4° C. to test the shelf life of the coating procedure at later time points.

Figure 2:
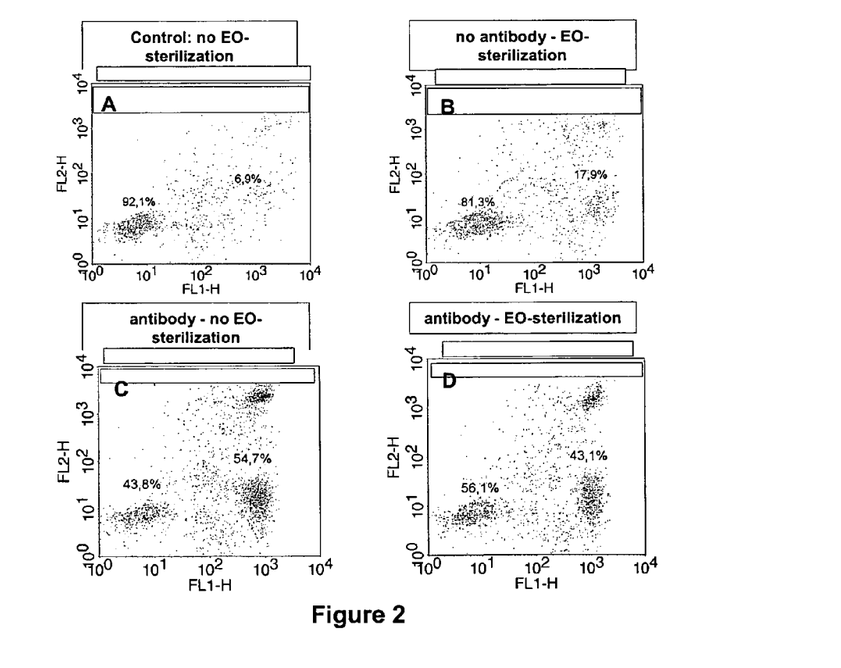

Results:

As representatively depicted in FIG. 2 the percentage of Jurkat cells undergoing spontaneous apoptosis (A) was 6.9% (range: 6-8%). Jurkat cells challenged with coated wells that underwent sterilization in the absence of immobilized antibodies (B) exhibited slightly enhanced apoptosis (17.9%; range: 16-20%). Anti-Fas, immobilized according to the above described coating procedure (C), induced apoptosis in 54.7% of the cells (range: 54-58%). After sterilization with ethyleneoxide (EO) the antibody-mediated induction of apoptosis (D) in Jurkat cells was 43.1% (range: 40-44%). The EO-mediated reduction of antibody function thus was approximately 25% compared to the unsterilized control (procedure without EO gas). Dot blot analyses (FIG. 2) show the fluorescence distribution for the respective cell population (FL1=apoptosis; FL2=necrosis).

Example 2: Production of a Leukocytes Inhibition Module (LIM)

For producing a LIM, a foam was soaked in a mixture of 98% methanol and 2% (3-glycidyl-oxypropyl)trimethoxysilane (Sigma) for 20 minutes and then dried, followed by an incubation of 100 µg antibody in a buffer consisting of 15 mM sodium carbonate and 35 mM sodium hydrogencarbonate in water (ph 9) for 2 h at 37° C. Alternatively, PBS can be used as buffer for the antibody. After that, addition of isotonic NaCl solution including 2% human albumin protein concentration is done with another 1 h incubation. Subsequently 10 washing cycles using isotonic sodium chloride-solution containing 1% human albumin are performed. At least, incubation with isotonic sodium-solution containing 5% human albumin and 5% mannitol for 30 min is followed by drying. Ethylenoxide-sterilization diminished the antibody activity (tested with Jurkat cells) for about 60%. After β-radiation using an electron accelerator with 10 MeV with a dose of 25 kGray the antibody activity was preserved to about 70% compared to the activity without sterilization. Alternatively, the sterilization may be effected using γ-radiation, e.g. using a Co$^{60}$ source.

A scheme of a LIM is depicted in FIG. 4.

The invention claimed is:

1. A method of producing a solid coated carrier carrying a biological material, comprising the sequential steps of:
    (a) incubating a solid carrier with a solution comprising 0.1 to 10% (w/w) or (v/v) of at least one silane and subsequently removing the solution, wherein the at least one silane is selected from the group consisting of alkoxysilanes, organofunctional silanes, hydrogensiloxanes, siloxanes and organosilanes comprising silyl compounds with other functional groups;
    (b) attaching the biological material to the carrier by incubating the carrier with an aqueous solution containing the biological material and having a salt content of less than 0.9% (w/w) and subsequently removing the aqueous solution, wherein the biological material is selected from the group consisting of polypeptides and proteins, wherein the biological material is directly attached to the solid carrier by a covalent bond or noncovalent bond, or indirectly attached to the solid carrier by forming a covalent bond with the at least one silane that is bound to the solid carrier;
    (c) incubating the carrier in an aqueous solution consisting essentially of one or more substances selected from (poly)peptides, polyalcohols and a mixture thereof, wherein the polyalcohols are selected from the group consisting of sorbitol, mannitol, glycerol, and xylitol; and
    (d) sterilizing the produced solid coated carrier.

2. The method according to claim 1, further comprising a step (c') subsequent to the step (c) and previous to step (d):
    (c') air drying the carrier until the residual water content is <20% (w/w).

3. The method according to claim 1, further comprising a step (a') subsequent to step (a) and previous to step (b):
    (a') air drying the carrier until the residual content of the solution is less than 10% of the originally applied solution.

4. The method according to claim 1, further comprising a step (b') subsequent to the step (b) and previous to step (c):
(b') incubating the carrier in a buffered aqueous solution containing a blocking agent and removing the aqueous solution.

5. The method according to claim 1 further comprising a step (b") subsequent to the step (b) and previous to step (c):
(b") blocking unbound binding sites using an aqueous solution containing 0.5-10% (w/w) substances selected from the group consisting of (poly)peptides, hydroxyethylstarch (HES), mannitol, sorbitol, polyethyleneglycol (PEG), and milk, soya, wheat or egg derived protein and optionally performing one or more washing steps using an aqueous solution after blocking.

6. The method according to claim 1, wherein the carrier in step (c) is incubated in an aqueous solution consisting essentially of one or more of albumin, mannitol, or sorbitol.

7. The method according to claim 1, wherein the material of the carrier is of porous structure.

8. The method according to claim 7, wherein the material of the carrier is characterized by a surface/gaseous volume ratio in a range of 30 $cm^{-1}$ to 300 $cm^{-1}$.

9. The method according to claim 7, wherein the material of the carrier is characterized by a material volume ratio between uncompressed and compressed porous material in a range of 4 to 40.

10. The method according to claim 7, wherein the material of the carrier has the structure of hollow fiber characterized by a material volume ratio between uncompressed and compressed porous material in a range of 1 to 10 and/or a surface/gaseous volume ratio is in a range of 200 $cm^{-1}$ to 2000 $cm^{-1}$.

11. The method according to claim 1, wherein the material of the carrier is selected from the group consisting of glass, polyurethane, polyester, polysulfone, polyethylene, polypropylene, polyacrylic, polyacrylonitrile, polyamide, PMMA, fleece wadding, open porous foam plastic, open porous foam glass, reticular plastic, reticular glass, and structures derived from marine sponges (porifera).

12. The method according to claim 1, wherein the solution in step (a) is an aqueous solution.

13. The method according to claim 1, wherein the solution in step (a) is a non-aqueous solution.

14. The method according to claim 1, wherein the at least one silane is selected from the group consisting of alkoxysilanes, hydrogensil(ox)anes, siloxanes and organosilanes comprising silyl compounds which contain one or more functional groups.

15. The method according to claim 1, wherein the polypeptide in step (b) is a receptor.

16. The method according to claim 15, wherein the receptor is an antibody, an antibody fragment or antibody derivative.

17. The method according to claim 16, wherein the antibody is a monoclonal antibody.

18. The method according to claim 16, wherein the antibody is of the IgG, IgY or IgM class.

19. The method according to claim 1, wherein the biological material is attached to said carrier in step (b) via a covalent bond.

20. The method according to claim 1, wherein the steps (a) to (c) are carried out in one or more tubes which comprise the carrier, wherein the tubes are rotated around an axis.

21. The method according to claim 1, wherein the solutions are re-circulated by using a pump.

22. The method according to claim 7, wherein the carrier made of a material having a porous structure comprises at least one further material.

23. The method according to claim 22, wherein the at least one further material is selected from the group consisting of carbon, $SiO_2$, HES and biotin.

24. The method according to claim 1, wherein the sterilization of the produced solid coated carrier is effected by ethyleneoxide (EO), beta radiation, gamma radiation, X-ray, heat inactivation, autoclaving or plasma sterilization.

25. The method of claim 1, wherein the aqueous solution of step (b) is a buffered aqueous solution.

26. The method of claim 1, wherein for (b) the aqueous solution is buffered and has a salt content of less than 0.2% w/w.

27. The method of claim 1, wherein the at least one silane comprises a functional group that can form a covalent bond with the biological material.

28. A method of producing a solid coated carrier carrying biological material, consisting of the steps of:
(a) incubating a solid carrier with a solution comprising 0.1 to 10% (w/w) or (v/v) of at least one silane and subsequently removing the solution and drying the carrier until the residual content of the solution is less than 10% of the originally applied solution, wherein the at least one silane is selected from the group consisting of alkoxysilanes, organofunctional silanes, hydrogensiloxanes, siloxanes and organosilanes comprising silyl compounds with other functional groups;
(b) attaching the biological material to the carrier by incubating the carrier with a solution containing the biological material and subsequently removing the aqueous solution, wherein the biological material is selected from the group consisting of (poly)peptides, peptides and proteins, and wherein the solution has a salt content less than 0.9% w/w, wherein the biological material is directly attached to the solid carrier by a covalent bond or noncovalent bond, or indirectly attached to the solid carrier by forming a covalent bond with the at least one silane that is bound to the solid carrier;
(c) incubating the carrier in a buffered aqueous solution containing a blocking agent and removing the aqueous solution;
(d) incubating the carrier in an aqueous solution comprising one or more substances selected from (poly)peptides, polyalcohols, or a mixture thereof, wherein the polyalcohols are selected from the group consisting of sorbitol, mannitol, glycerol, and xylitol, whereby the biological material is embedded in a coating layer and air-drying the carrier until the residual water content is <20% (w/w); and
(e) sterilizing the produced solid coated carrier.

29. The method of claim 28, wherein the solution containing the biological material is a buffered aqueous solution.

* * * * *